(12) United States Patent
Cheng et al.

(10) Patent No.: US 10,732,141 B2
(45) Date of Patent: Aug. 4, 2020

(54) ELECTROCHEMICAL GAS SENSOR SYSTEM WITH IMPROVED ACCURACY AND SPEED

(71) Applicant: InSyte Systems, Newark, CA (US)

(72) Inventors: Jim Chih-Min Cheng, Fremont, CA (US); Eric Paul Lee, Mountain View, CA (US); Jerome Chandra Bhat, Palo Alto, CA (US)

(73) Assignee: InSyte Systems, Newark, CA (US)

( * ) Notice: Subject to any disclaimer, the term of this patent is extended or adjusted under 35 U.S.C. 154(b) by 143 days.

(21) Appl. No.: 15/897,034

(22) Filed: Feb. 14, 2018

(65) Prior Publication Data

US 2018/0231494 A1    Aug. 16, 2018

Related U.S. Application Data

(60) Provisional application No. 62/459,597, filed on Feb. 15, 2017.

(51) Int. Cl.
*G01N 27/407* (2006.01)
*G01N 33/00* (2006.01)
*G01N 27/404* (2006.01)

(52) U.S. Cl.
CPC ..... *G01N 27/4074* (2013.01); *G01N 27/4045* (2013.01); *G01N 27/4071* (2013.01); *G01N 27/4076* (2013.01); *G01N 33/0013* (2013.01)

(58) Field of Classification Search
CPC ........................ G01N 27/4075; G01N 27/4071
See application file for complete search history.

(56) References Cited

U.S. PATENT DOCUMENTS 4,894,138 A    1/1990  Gambert et al.
4,961,834 A   10/1990  Kuhn et al.
(Continued)

FOREIGN PATENT DOCUMENTS

WO    2007149471 A2    12/2007

OTHER PUBLICATIONS

EPO as ISA for PCT/US2018/018306, "International Search Report and Written Opinion", 20 pages.
(Continued)

*Primary Examiner* — Luan V Van
*Assistant Examiner* — Caitlyn Mingyun Sun
(74) *Attorney, Agent, or Firm* — Patent Law Group; Brian D. Ogonowsky

(57) ABSTRACT

An electrochemical cell for sensing gas has added mechanical support for the working electrode to prevent flexure of the working electrode due to pressure differentials. The added mechanical support includes: 1) affixing a larger area of the working electrode to the body of the cell; 2) a gas vent to a cavity of the body to equalize pressures; 3) a rigid electrolyte layer abutting a back surface of the working electrode; 4) infusing an adhesive deep into sides of the porous working electrode to enhance rigidity; 5) supporting opposing surfaces of the working electrode with the rigid package body; and 6) other techniques to make the working electrode more rigid. A bias circuit is also described that uses a controllable current source, an integrator of the varying current, and a feedback circuit for supplying a voltage to the counter electrode and a bias voltage to the reference electrode.

15 Claims, 4 Drawing Sheets

(56) References Cited

U.S. PATENT DOCUMENTS

| | | | |
|---|---|---|---|
| 6,376,124 B1 | 4/2002 | Dodgson et al. | |
| 8,815,065 B2 * | 8/2014 | Yamamoto | G01N 27/4072 204/415 |
| 9,989,492 B1 | 6/2018 | Cheng et al. | |
| 2005/0034987 A1 | 2/2005 | Zhou et al. | |
| 2014/0311905 A1 * | 10/2014 | Stetter | C09D 11/52 204/424 |
| 2015/0226585 A1 * | 8/2015 | Yang | G01D 11/30 73/431 |
| 2015/0241375 A1 | 8/2015 | Merz et al. | |
| 2015/0346138 A1 | 12/2015 | Allen et al. | |
| 2016/0041114 A1 | 2/2016 | Neel et al. | |
| 2016/0073930 A1 * | 3/2016 | Stetter | A61B 5/082 600/532 |
| 2016/0178565 A1 | 6/2016 | Chapples et al. | |
| 2016/0349205 A1 | 12/2016 | Stetter et al. | |
| 2017/0336343 A1 | 11/2017 | Bhat et al. | |

OTHER PUBLICATIONS

EPO as ISA PCT/US2017/033649, "International Search Report and Written Opinion", dated Oct. 2, 2017, 25 pages.

Stetter et al., "Amperometric Gas Sensors—A Review", Chemical Reviews, vol. 108, No. 2, Jan. 18, 2008, pp. 352-366, 15 pages.

SGX Sensortech, "Electrochemical Sensors Application Note 2 Design of Electronics for Electrochemical Gas Sensors", pp. 1-5, England.

Dryden et al., "DStat: A Versatile, Open-Source Potentiostat for Electroanalysis and Integration", Oct. 28, 2015, 11 pages, <http://journals.plos.org/plosone/article?id=10.1371/journal.pone.0140349>.

Electronics Tutorials, "The Integrator Amplifier", 6 pages, <http://www.electronics-tutorials.ws/opamp/ppamp_6.html>.

Unpublished U.S. Appl. No. 62/620,963, "Low Impedance Sensor for Low Density Material", filed Jan. 23, 2018.

Unpublished U.S. Appl. No. 62/620,685, "Gas Diffusion Electrode and Membrane Electrode Assembly", filed Jan. 23, 2018.

* cited by examiner

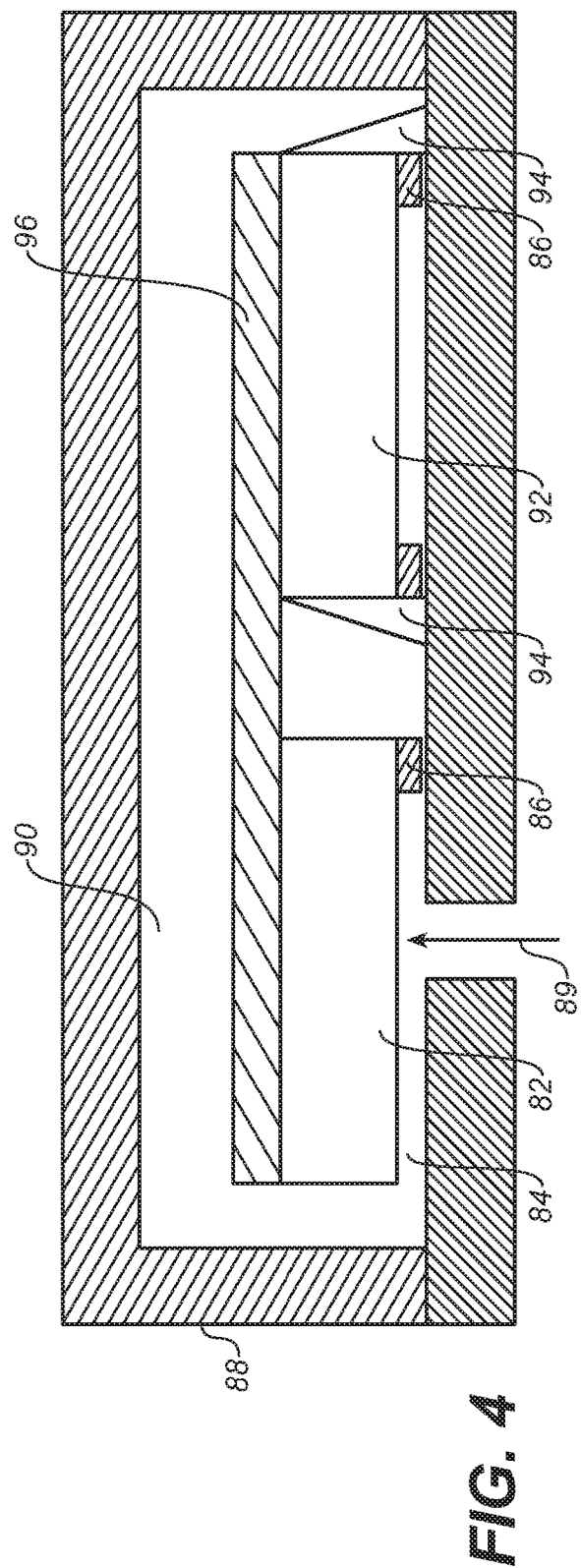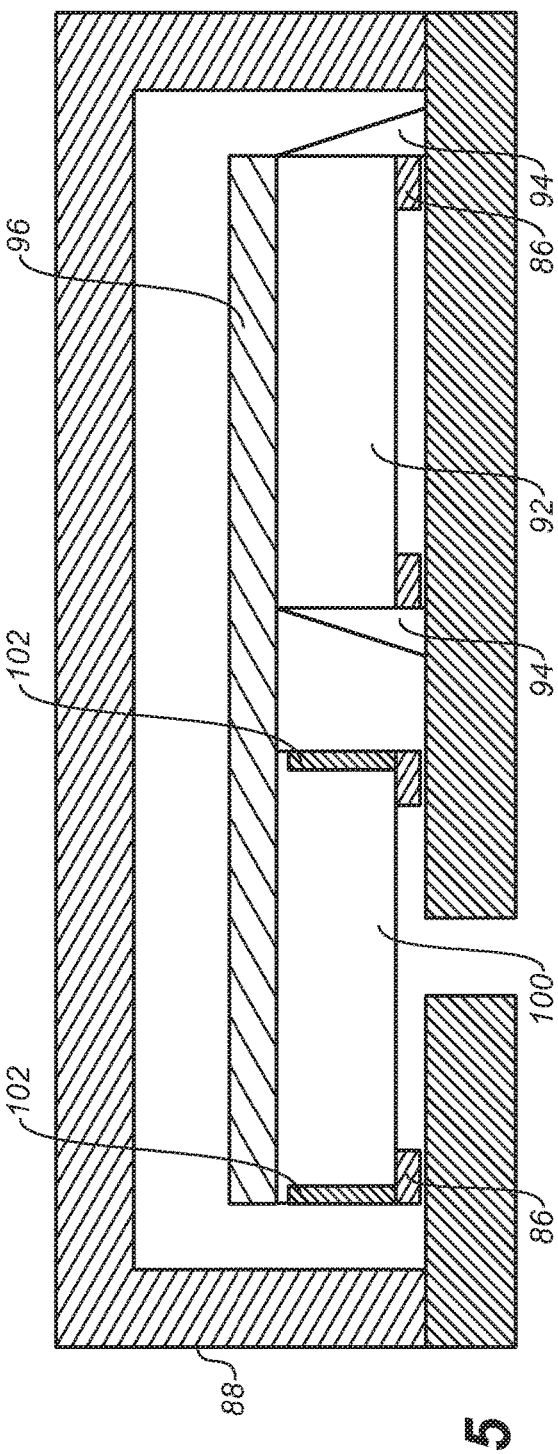

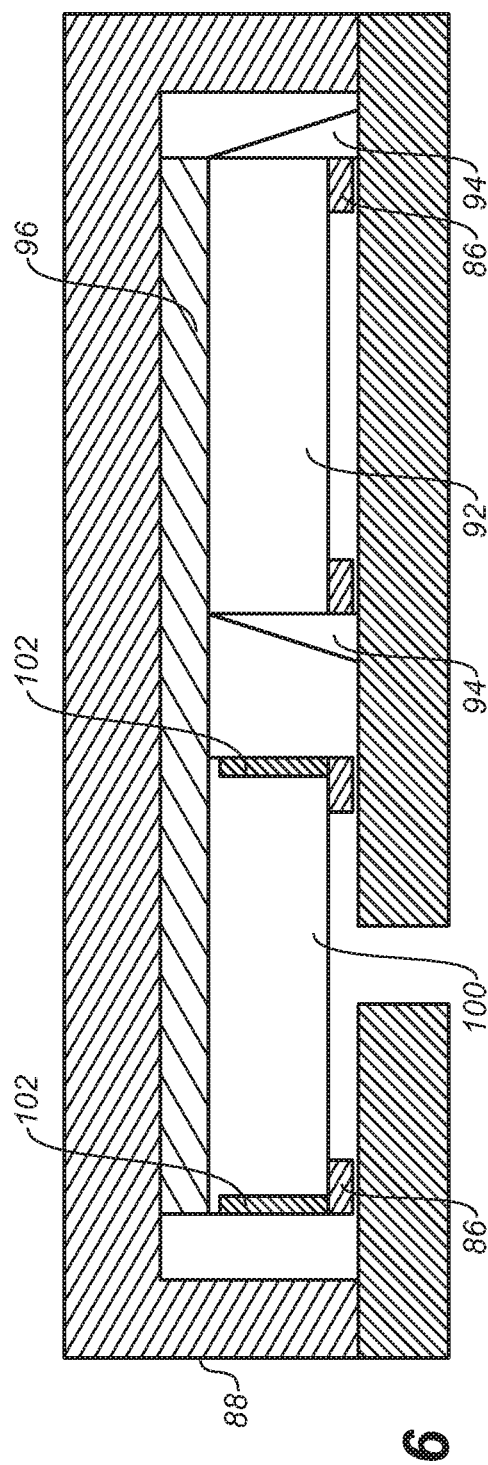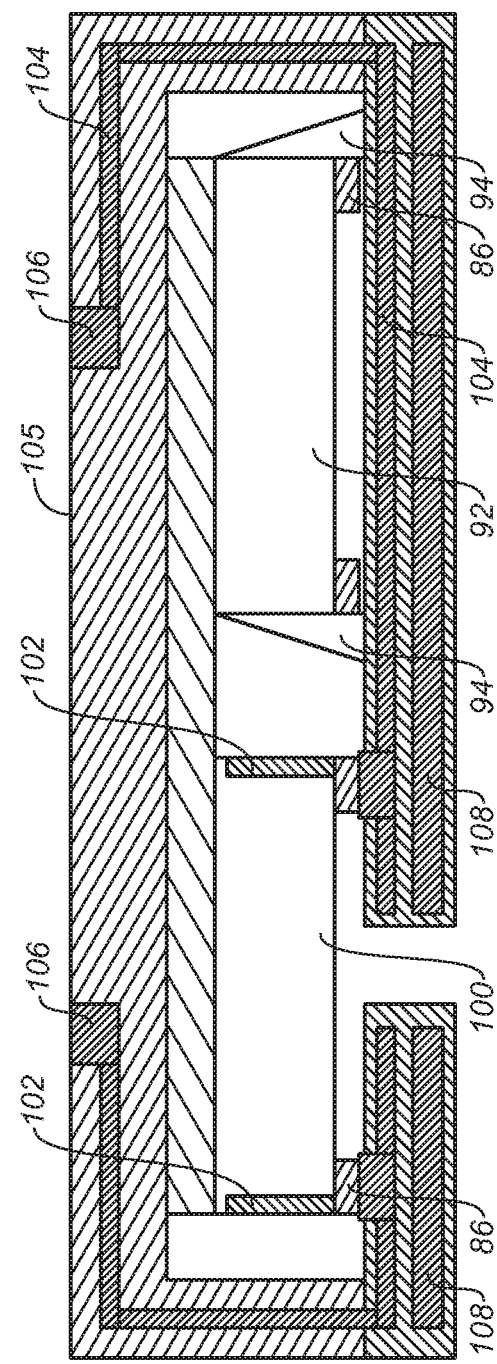

ELECTROCHEMICAL GAS SENSOR SYSTEM WITH IMPROVED ACCURACY AND SPEED

CROSS-REFERENCE TO RELATED APPLICATIONS

This application is based on and claims priority from U.S. provisional patent application Ser. No. 62/459,597, filed on Feb. 15, 2017, by Jim Chih-Min Cheng et al., assigned to the present assignee and incorporated herein by reference.

FIELD OF THE INVENTION

This invention relates to the sensing and identification of gasses by an electrochemical cell in conjunction with a sensing circuit and, in particular, to techniques for reducing flexure of a working electrode and an improved biasing circuit.

BACKGROUND

Given the dramatic changes in the earth's atmosphere, precipitated by industrialization and natural sources, as well as the dramatically increasing number of household and urban pollution sources, the need for accurate and continuous air quality monitoring has become necessary to both identify the sources and warn consumers of impending danger. Tantamount to making real-time monitoring and exposure assessment a reality is the ability to deliver, low cost, small form factor, and low power devices which can be integrated into the broadest range of platforms and applications.

There are multiple methods of sensing distinct low density materials such as gasses. Common methods include gas chromatography, nondispersive infrared spectroscopy (NDIR), the use of metal oxide sensors, the use chemiresistors, and the use of electrochemical sensors. The present invention pertains to electrochemical sensors. The principle of operation of an electrochemical sensor is well known and is summarized in the following overview: http://www.spec-sensors.com/wp-content/uploads/2016/05/SPEC-Sensor-Operation-Overview.pdf, incorporated herein by reference.

Basically, in an electrochemical sensor, a porous sensor electrode (also known as a working electrode) contacts a suitable electrolyte. The gas permeates the electrode and contacts the electrolyte. The sensor electrode typically comprises a catalytic metal that reacts with the target gas and electrolyte to release or accept electrons, which creates a characteristic current in the electrolyte when the electrode is properly biased and when used in conjunction with an appropriate counter-electrode. The current is generally proportional to the amount of target gas contacting the sensor electrode. By using a sensor electrode material and bias that is appropriate for the particular gas to be detected, the concentration of the target gas in the ambient atmosphere can be determined from the sensing current.

The sensitivity of an electrochemical cell to a particular gas may be impacted by the application of a bias voltage to that cell. Therefore, by applying a set of different biases to an electrochemical cell, and comparing the recorded signal to a library of signals (in a look-up table) corresponding to those signals characteristic of individual known gasses, it is possible to ascertain the presence of, differentiate between, and quantify the occurrence of multiple gasses in the environment of the sensor. By continuously and quickly ramping the bias applied to the cell, a single electrochemical cell may rapidly differentiate between multiple gasses in its environment. Identification of an analyte in a controlled environment, such as that of a laboratory, via a potential ramping scheme is known in the art as "voltammetry". However, electrochemical sensing systems known in the art are limited with respect to the speed at which voltammetry may run due to a combination of the electrochemical cells having large resistance-capaciotance (RC) time constants and the drive electronics having long settling times, resulting in voltammetry measurements taking up to 20 minutes or even more. Ramping the bias voltage at only a few millivolts per second is typical.

In the event that such a measurement is performed in a highly controlled environment, such a long data collection time is of no consequence since the test conditions may be controlled over that timeframe. However, outside of a controlled laboratory environment, the ambient conditions of the cell may change significantly over the course of such an extended period of data collection. For example, in an everyday consumer use case, the ambient relative humidity, the ambient temperature, and the ambient mixture and concentrations of analyte gasses may change significantly over such an extended data gathering period. All these factors combined with electronic drift inherent to running voltammetry on the electrochemical cell render analysis of the data meaningless. Further, if the gas sensor is intended detect dangerous gasses, the long delay time may result in a harmful effect.

Accordingly, for such a consumer application, an electrochemical gas sensor is required having small form factor, and hence a small time constant, such as described in the Applicant's U.S. patent application Ser. No. 15/598,228, in conjunction with a novel drive circuit enabling short settling times. Such a system enables voltammetry to be performed in a period of a few seconds or less. Over such a timescale, the ambient conditions in a majority of uncontrolled consumer environments in which the cell may be present would be essentially invariant, resulting in the ability to perform voltammetry in an essentially uncontrolled environment whilst providing data of sufficient quality to enable accurate electrochemical analysis.

The varying bias voltage may be sinusoidal or have another waveform. It is common to supply the variable bias voltage via a digital-to-analog converter (DAC) that outputs a varying voltage. Such an output contains discrete steps due to the quantized nature of the DAC output, and thus there is a high $dv/dt$. The rate at which the bias may be ramped in an electrochemical cell is limited, among other factors, by the capacitance of the cell, and the presence of current spikes occurring within the cell during the step-wise application of the bias ramp to the cell. The impact of the capacitive nature of the cell on the current spikes occurring during a voltage step is described by the equation $i=C\,dv/dt$. Excessive transient currents can lead to damage of the cell. In certain schemes, accurate measurement of the cell requires for the transient currents to have mostly decayed so that the cell output is measured while in its steady-state condition. Accordingly, a settling time typically occurs between the point at which a voltage step is applied to the cell and the point at which the current generated at the working electrode of the cell is measured. This limits the rate at which a bias sweep of the cell may be applied. Minimizing the capacitance of the cell and occurrence of current spikes within it allows for maximizing the rate at which voltammetry may be performed, hence maximizing performance of the sensor.

Electronic noise is also an important issue in electrochemical sensors which affects accuracy and speed achievable by the sensors. Electrochemical sensors are known for picking up 60 Hz and a variety of RF noise due to the large electrodes and electrolytes. Commercial systems can minimize the noise through shielded housings around the sensors, powering the sensor using a battery, and using signal processing to filter out the noise. However, noisy environments still generally limit the accuracy of the electrochemical systems and size of the systems due to the extra electronics needed to minimize the noise. This impacts the rate at which the ramps of the voltammetry can be executed at due to higher current spikes and longer settling times which can occur during step transitions due to the additional circuit elements, such as resistors and capacitors, which need to be added to mitigate noise.

Additionally, any flexure of the working electrode changes its electrical characteristics. Flexure may occur due to gas pressure fluctuations. Pressure built up due to small pore size in the electrode can also change the position/formation of the three phase interface inside the electrode which can impact the sensitivity of the sensor. The three phase interface is a critical aspect of a gas diffusion electrode and is formed at the conjunction interface of a gas, solid, and liquid (i.e., gas/electrode/electrolyte). A change in pressure could influence the density of the three-phase interface and where the three-phase interface is formed.

Accordingly, what is needed is an electrochemical sensor system for gasses that employs a varying bias signal that does not have high dv/dt characteristics. What is also needed is an electrochemical sensor that is less susceptible to noise. Additionally, an electrochemical sensor where the working electrode does not substantially flex due to changing gas pressures is required for stability in changing environments. Further, a control method is desired for use with a low capacitance gas sensor that can quickly detect a variety of different gasses in a short time.

SUMMARY

A sweeping bias voltage generator is disclosed that applies a varying bias voltage to an electrochemical sensor, where the bias voltage may be sinusoidal or ramping without any steps, so is continuous. Therefore, current spikes are negligible due to i=C dv/dt. As a result, little or no settling time is needed, and the sensor can have a very rapid response to changing ambient gasses.

To minimize flexure of the working electrode, mechanical support features of the working electrode are disclosed that prevent the working electrode being distorted due to changing gas pressures. Additionally, a sensor structure is described that equalizes the gas pressure on the opposing surfaces of the working electrode to prevent flexure.

To minimize electronic noise, conductors and metal shielding are embedded in the walls of the sensor body (e.g., molded ceramic), which prevent impact of noise to the system. Embedding the conductors and shielding protects the metal and prevents corrosion due to electrolyte (e.g., acid) contact and environmental exposure. This also allows for simplification of circuit design, allows for minimal integrated circuit size (so the circuit can be integrated with the sensor), and allows for simplification of post-processing due to less noise.

Uses of the sensor module include detection of air quality (e.g., carbon monoxide), gas exposure control, toxic gas detection, breath analysis, feedback in industrial processes, etc.

Other embodiments and advantages are described.

BRIEF DESCRIPTIONS OF DRAWINGS

FIG. 4 is a cross-section of a portion of an electrochemical cell where an incoming gas is allowed to pressurize a cavity in the body to equalize the pressures on opposing surfaces of the WE.

FIG. 5 is a cross-section of a portion of an electrochemical cell where a rigid electrolyte layer mechanically supports the back surface of the WE to prevent flexure of the WE, where the sides of the WE are sealed to prevent the gas exiting from the sides of the porous WE, and where the sides of the counter electrode (CE) are also sealed to prevent gas from entering the sides of the CE.

FIG. 6 is a cross-section of an electrochemical cell where the rigid packaging body itself is used to mechanically support the back surface of the WE so as to prevent flexure.

FIG. 7 is a cross-section of an electrochemical cell with an integrated shield layer and conductors for routing signals to the electrodes. The shield layer and conductors are completely encased within walls of the package body. The conductors terminate in metal pads for bonding to a printed circuit board.

Elements that are the same or equivalent in the various figures are labeled with the same numeral.

DETAILED DESCRIPTION

Figure 1:
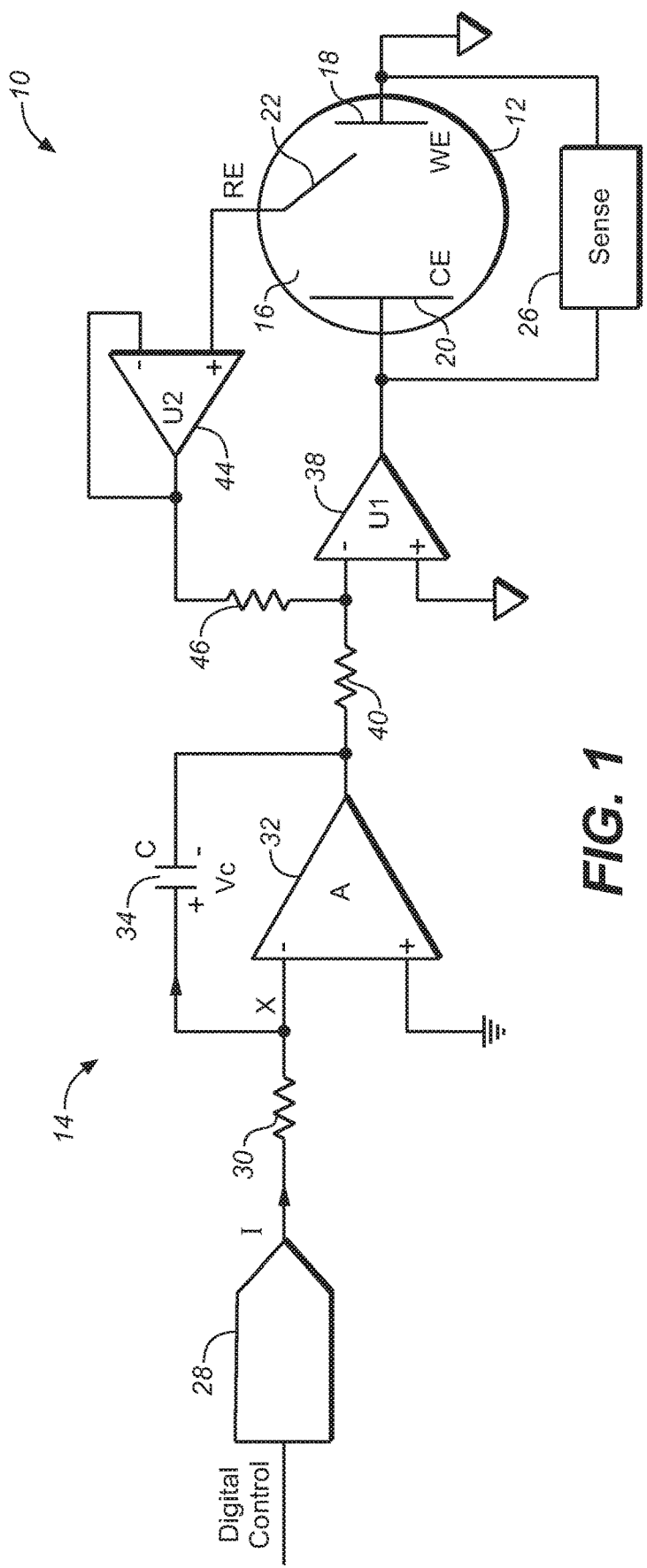
FIG. 1 illustrates a bias circuit coupled to an electrochemical cell in accordance with one embodiment of the invention.

FIG. 1 illustrates an electrochemical sensor module 10, showing a cell 12 and a bias circuit 14 for sweeping a bias voltage to allow the cell 12 to detect different types of gasses. The cell features are designed so that the cell 12 can detect different types of gasses in response to different bias voltage levels. The voltage should be swept as rapidly as practical to more quickly identify the presence of a target gas, which may be a harmful gas.

Basically, the cell 12 contains a cavity 16 containing an electrolyte that is in contact with a working electrode (WE) 18, a counter electrode (CE) 20, and a reference electrode (RE) 22. Additional electrodes can be added as additional working and counter electrodes for different variants of the cell for gas detection. The RE 22 provides a means by which a reference potential may be applied to the cell.

The body of the cell 12 includes a gas opening to allow diffusion of the gas or atmosphere being sensed into the porous WE 18. In certain embodiments, the opening is partially or fully filled with a porous material which allows gas to diffuse into the WE 18 but blocks the liquid or paste-like electrolyte from exiting the cavity.

The electrodes 18/20/22 may comprise an electrically conducting material, such as carbon, and a catalyst such as ruthenium, copper, gold, silver, platinum, iron, ruthenium, nickel, palladium, cobalt, rhodium, iridium, osmium, vanadium, or any other suitable transition metal and their alloys. The catalyst is selected so as to react with one or more particular gases. The electrodes 18/20/22 may be partially permeable to both the electrolyte and the gas to be detected so that the electrochemical reaction may occur within the body of the electrodes 18/20/22.

The electrolyte may comprise an ionic material such as an acid. The electrolyte may be viscous such as a gel, or may be a polymer infused with an organic or inorganic acid.

The bias circuit 14 applies electrical potentials between the WE 18, CE 20, and RE 22. A sensing circuit 26 senses electrical currents passing between the WE 18, CE 20, and RE 22, and reports on the sensed signals. The sensing circuit 26 may comprise a trans-impedance amplifier (TIA) in conjunction with an analog-to-digital converter (ADC) capable of converting the sensed signal from the working electrode into a digital representation. The digital signals are processed by a microprocessor on which algorithms may be stored and executed enabling, for example, reporting out of calibrated gas concentrations. The sensing circuit 26 and its connections to the electrodes may be conventional.

In an example, when a toxic gas such as carbon monoxide (CO) comes in contact with the WE 18 (the sensing electrode), oxidation of CO gas will occur on the WE 18 through chemical reaction with water molecules in the air. Connecting the WE 18 and the CE 20 through a potentiostat circuit will allow protons (H+) generated on the WE 18 to flow toward the CE 20 through the electrolyte (an ion conductor). In addition, generated electrons move to the CE 20 through the potentiostat circuit. A reaction with oxygen will occur on the CE 20 to reform water. By measuring the level of current between the WE 18 and the CE 20, the electrochemical cell 12 can detect the concentration of the target gas (e.g., CO) in the air. This is usually done at a single bias point. Different types of electrodes and different bias voltages traditionally have been used to detect different types of gases.

FIG. 1 illustrates a bias circuit (a potentiostat) for use with an electrochemical cell, in accordance with one embodiment of the invention. The bias circuit supplies a variable bias signal to the RE 22.

A digital control signal is applied to the input of a current source 28 that converts the digital code to an analog current. The digital code may be constant or vary. A varying digital code may cause the current source 28 to output a substantially sinusoidal current. The current is applied, via an input resistor 30, to the inverting input of an op amp 32. The op amp 32 is connected as an integrator due to the feedback capacitor 34 being connected between the output and the inverting input. The non-inverting input is connected to ground. The feedback operates to cause the potential between the inverting and non-inverting inputs to approximately equal zero volts. The integration of the input current results in a continuous signal at the output of the op amp 32, even if the output of the current source 28 may be stepped. The output of the op amp 32 varies continuously as a function of the current output by the current source 28. Supplying a positive current by the current source 28 decreases the potential at the output of the op amp 32, and providing a negative current increases the potential at the output. Providing zero current maintains a constant output voltage. The output of the op amp 32 is a reverse integral (180° phase shift of the integral) of the input current. Step functions at the input do not cause discontinuities in the output voltage of the op amp 32.

The continuous output of the op amp 32 is then applied to the inverting input of an op amp 38, via a resistor 40, whose output is coupled to the CE 20. The non-inverting input of the op amp 38 is coupled to ground, and the feedback loop tries to keep the potential between the inverting and non-inverting inputs at zero volts.

The RE 22 is coupled to the non-inverting input of another op amp 44, whose inverting input is coupled to its output. The output of the op amp 44 is coupled to the inverting input of the op amp 38 via a resistor 46, the non-inverting input of the op amp 38 is connected to ground, and the feedback loop tries to keep the potential between RE 22 and the inverting input of op amp 38 at zero volts.

The op amp 44 is a unity gain amplifier. To the first order, the op amp 44 and its feedback loop have no impact on the circuit. In reality, op amps are non-ideal and have input leakage current. Input leakage current is typically larger into the inverting input of an op amp than it is into the non-inverting input. The role of op amp 44 is to reduce the input leakage current drawn from the RE 22. The RE 22 ideally applies a bias to the electrochemical cell, but does not draw a current. If it does so, it impacts the performance and state of the cell. The potentiostat circuit (based on op amp 38) works by changing the bias and current being driven through the CE 20 such that: (i) the RE 22 is held at the bias potential being applied at the inverting input to op amp 38, and (ii) the current required to support the electrochemical reaction occurring within the cell between the WE 18 and the CE 20 is provided to the cell.

Accordingly, the RE 22 of the electrochemical cell 12 is properly biased at a varying (e.g., ramping) continuous signal for operating the gas sensor. The RE 22 can be biased at any voltage. The circuit allows the potential of the CE 20 to vary as required to enable the required current to flow between the CE 20 and the WE 18. This is known as voltammetry. Suppression of discontinuities in the applied bias enables the sensor to be accurately controlled with minimized or completely eliminated transient signals that could negatively affect performance. The ramping may be performed rapidly to quickly detect a range of gasses in an uncontrolled environment. No settling time is needed. If a dangerous gas is detected, circuitry may be used to generate an alarm or turn off the source of the gas.

A capacitor (not shown) may optionally be coupled between the RE 22 and the CE 20 to filter high frequency signals.

The op amp 44 may be deleted by connecting a resistor divider between the RE 22 and the inverting input of the op amp 38, with a capacitor connected between the resistor nodes and the CE 20; or in parallel with the resistor divider.

There are various ways to detect the reaction of the sensor to the target gasses. The gas diffuses into the porous WE 18 where it is oxidized or reduced. This electrochemical reaction results in an electric current that passes through the external sense circuit 26. The bias circuit 14 maintains a bias voltage between the WE 18 and RE 22. At the CE 20, a counter half reaction occurs such that the electrons generated or consumed at the WE 18 equals the electrons generated or consumed at the CE 20. Additionally, should the CE 20 be exposed to the environment instead of the WE 18, the CE 20 will run the forward reaction while the WE 18 will run the reverse reaction. In gas sensing, it is rare for the CE 20 to face the environment, though such a configuration is known to be possible.

The magnitude of the current is controlled by how much of the target gas is reacted at the WE 18 so that the output from the sensor is linearly proportional to the gas concentration. Accordingly, the sense circuit 26 measures the current and may perform an analysis to associate the current to the bias voltage and to the target gas being presently measured.

Since the bias circuit 14 is current-controlled rather than voltage controlled, there are no current spikes due to capacitance (so no transient settling time) and the sensor can operate to rapidly detect the presence of various target gasses.

In one embodiment, the current source 28 and the electrical components are selected to vary the applied bias between 1V and −1V. The bias voltages may also be greater than 1V, such as up to 2.5V, and less than −1V, such as down to −2.5V. Some target gases, such as ethylene oxide, may require even higher bias levels for its oxidation depending on the electrode/electrolyte combination chosen, while some gases, such as carbon monoxide, only require a relatively low bias level. Some gases even oxidize at multiple bias levels. The two gases may be differentiated based on the varying bias levels needed to react the gasses at the WE 18. In more convoluted cases where the two gases have very similar bias levels, a more detailed voltammogram can be created by sweeping a number of bias points.

The bias circuit 14 and sensor 26 may be formed as a single integrated circuit.

The entire sensor may use a footprint of less than 10 mm×10 mm.

A novel drive scheme is also disclosed. To identify a single gas, or multiple mixed gasses, multiple biases are applied to the RE 22. Since different reactions are promoted or suppressed at different applied biases, it is possible to identify a particular gas by looking at the "spectrum" of the gas registered during the application of multiple bias points.

In the case of multiple gasses being present, in theory, the recorded spectrum of the gas mixture comprises the linear summation of the spectra of the individual component gasses, scaled by their relative concentrations and sensitivities. By comparing the captured spectrum to a reference library of gas spectra, it should be possible to identify the multiple gasses present.

Similar gasses will have similar peaks in the recorded spectra. For example, methanol and ethanol comprise similar chemical bonds, hence may have similar spectra which may have substantial overlap during any one particular bias sweep. Whereas it is known in the art that changing the waveform of an applied bias to an analyte may change the position of the recorded peaks, it is typically difficult to practically implement due to the limited bias ramp rates which may be successfully applied to typical electrochemical systems. This principle is known for liquid spectroscopy applications, though to the best of the inventors' knowledge, not yet demonstrated for electrochemical spectroscopy for gases due to the limited hardware. Accordingly, in the case of an electrochemical cell enabling fast ramping of an applied bias, it is possible to greatly further differentiate between the two or more similar gasses by changing the applied bias waveform and especially the speed of bias ramp, dV/dt over and above that capability in standard electrochemical systems.

In addition to being able to determine the presence of chemicals, voltammetry enables the determination of the relative humidity, the temperature, and the ionic state of the electrochemical cell. These factors are known to impact the sensitivity of electrochemical cells to gasses the cell is exposed to. In standards and the current state-of-the-art, often one or more of the factors are bundled into the generic parameter of drift resultant of limited cell hardware and ability to generate the necessary waveforms for proper compensation. In the case of voltammetry performed in an uncontrolled environment but in the order of a few seconds or less and in which the ambient and internal state of the cell are therefore essentially constant, it is possible to determine the relative humidity, temperature and ionic state of the electrochemical cell at the time at which the cell is also being exposed to a gas. This data can therefore be used to compensate for the impact of these factors on the sensitivity of the cell to a gas, thereby improving the accuracy with which the system can identify and quantify gasses.

Data collected during calibration of the sensor in a controlled environment is stored in a local look-up table, such as located in the same integrated circuit as the bias circuit and microprocessor. Sensor characteristics (bias levels, sensor current, etc.) corresponding to known target gasses and environmental conditions are also stored. Changes in the detected environment relative to the calibration data are then used to determine the concentration of targeted gasses in the environment and other environmental factors as the bias voltage is swept. The gas readings may be compensated by the detected humidity, temperature, etc. to determine the concentration. Rather than the bias being swept over the prior art cycle time of, for example, 20 minutes or more, the cycle time using the present invention may be less than one minute. This enables the rapid detection of a variety of gasses during a stable environment.

The waveforms corresponding to the detection of target gasses in the environment may comprise overlapping gas signals. A microprocessor then differentiates the different gasses corresponding to the overlapping gas signals based on stored data and algorithms. The microprocessor may perform as an inference engine with a set of equations that identify gasses present.

Another feature of the sensor relates to techniques that reduce or eliminate any flexure of the WE 18. Flexure of the WE 18 in the presence of changing conditions will change the response of the WE 18 to the target gasses. Calibration is initially performed under ideal conditions, and the sensor readings will be skewed if they occur while the WE 18 is flexed relative to it calibration state. One cause of flexure is a gas pressure difference on the front and back surfaces of the WE 18.

Figure 2:
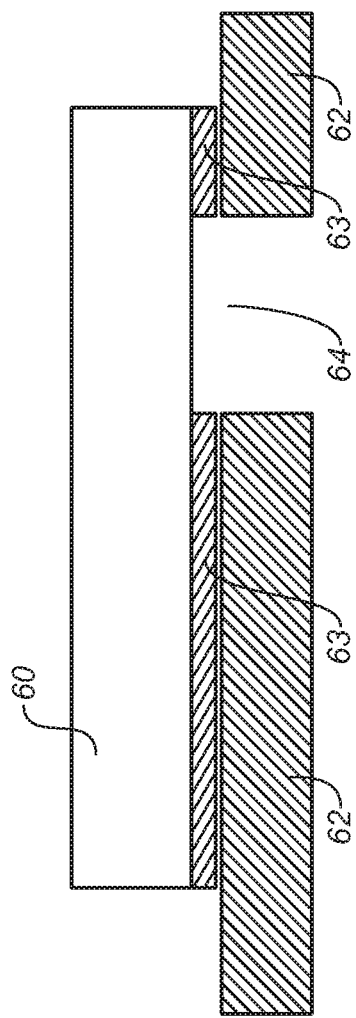
FIG. 2 is a cross-section of a portion of an electrochemical cell where the working electrode (WE) is affixed to the rigid body of the cell over a large area of the WE to prevent flexure of the WE.

FIG. 2 is a cross-sectional view of a portion of an electrochemical cell. A WE 60 is shown affixed to the rigid body 62 (e.g., ceramic) of the cell by an adhesive 63. The cell may be only a few millimeters in width and length. An opening 64 in the body 62 allows ambient gas to contact the WE 60. The WE 60 is porous, and the gas permeates through to an electrolyte (not shown) in contact with the back surface of the WE 60. The electrolyte carries charges between the CE (not shown) and the WE 60 to generate the currents that effectively identify the presence of the target gas.

The adhesive 63 also acts as a gas seal. The adhesive 63 may be epoxy, silicone, acrylate, or other adhesive, and may be conducting, for example via the inclusion of conducting metal, carbon, or other particles. If the adhesive 63 is conductive, it may serve to electrically connect the WE 60 to conductors that lead to metal pads for bonding to a printed circuit board. The entire front surface of the WE 60 except for the gas opening 64 area is affixed to the rigid body 62, so flexure of the WE 60 due to temperature fluctuations and pressure differentials is prevented. The WE 60 is also formed to be rigid to prevent flexure under normal operating conditions. The gas diffuses laterally and into the WE 60, so it is important that the adhesive 63 does not substantially diffuse into the WE 60. The adhesive 63 may be applied by printing or stamping onto the body 62. The electrolyte may be a liquid or gel contacting the back surface of the WE 60 so does not provide substantial mechanical support to the WE 60.

Figure 3:
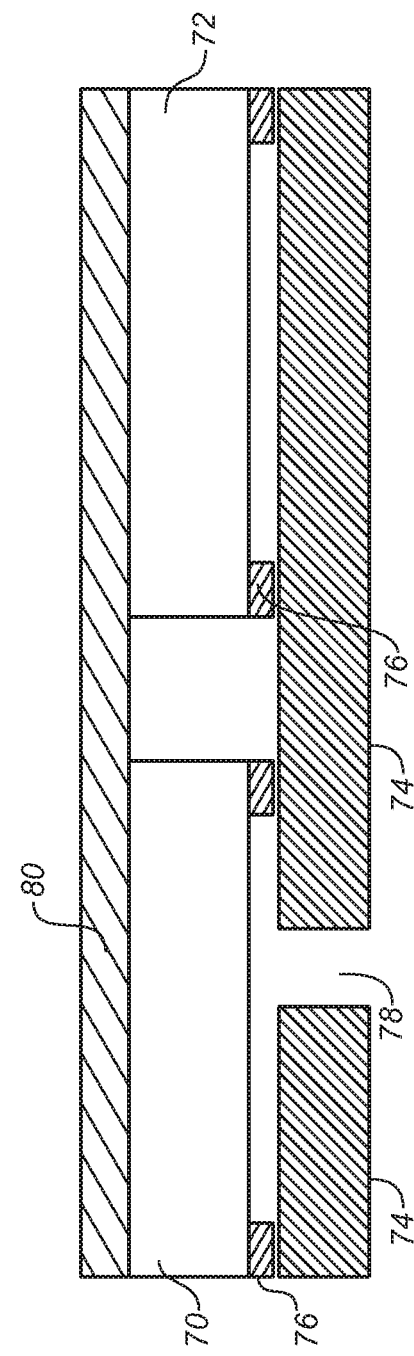
FIG. 3 is a cross-section of a portion of an electrochemical cell where a rigid electrolyte layer mechanically supports the back surface of the WE to prevent flexure of the WE.

FIG. 3 is a cross-sectional view of a portion of another electrochemical cell where a WE 70 and a CE 72 are affixed to the rigid body 74 of the cell via an adhesive 76. The adhesive 76 may be conducting to connect the electrodes to metal pads on the body 74. An opening 78 in the body 74 allows ambient gas to diffuse into the WE 70. Unlike in FIG. 2, the adhesive 76 is only applied to a perimeter portion of the WE 70. This allows the gas to enter a small sealed cavity between the WE 70 and the body 74 to diffuse into a larger area of the WE 70 sooner for a faster reaction time. The adhesive 76 blocks the gas from contacting the CE 72. Thus, the adhesive 76 itself does not substantially inhibit flexure of the WE 70.

The flexure of the WE 70 and CE 72 is inhibited by a fairly rigid electrolyte layer 80 that contacts the back surfaces of the WE 70 and the CE 72. The electrolyte layer 80 may be a rigid but porous polymer that is infused with an ionic material, such as sulfuric acid or phosphoric acid. The electrolyte layer 80 is sufficiently thick and rigid to prevent flexure of the WE 70 and CE 72 under normal operating conditions. Charges are free to move between the WE 70 and CE 72 through the electrolyte layer 80 to create the current signature of the target gas under the proper biasing conditions. The electrolyte layer 80 essentially forms an ion bridge between the electrodes. The electrolyte layer 80 may diffuse up to 10 microns or more into the porous WE 70 and CE 72 for good contact. Note that there may be a pressure differential between the gas on opposing surfaces of the WE 70, and such a pressure differential is not sufficient to flex the WE 70 due to the rigidity of the electrolyte layer 80.

FIG. 4 is a cross-sectional view of a portion of an electrochemical cell where the back and front surfaces of the WE 82 are exposed to the same gas pressure due to an opening 84 in the adhesive 86. The adhesive 86 may extend around almost the entire perimeter of the WE 82 for good mechanical support, but just needs to have a small opening to equalize the gas pressures. The body 88 may be ceramic. Since the target gas 89 enters the back cavity 90 of the body 88, the CE 92 must be sealed from the back cavity 90 with an adhesive or sealant 94, such as epoxy. An electrolyte layer 96 may be a porous material infused with an electrolyte, such as an acid, for transporting charge between the WE 82 and the CE 92. The electrolyte layer 96 may be sufficiently non-porous to gasses so as to prevent the gas 89 in the back cavity 90 from diffusing into the electrolyte and reacting with the back surface of the WE 82. If such "back" diffusion took place, the sensor would take a long time to react to changes in the ambient air.

In a variation of FIG. 4, the bottom surface perimeter of the WE 82 is completely sealed by the adhesive 86, and the gas 89 is allowed to diffuse laterally through the highly porous WE 82 and exit an edge of the WE 82 to enter the back cavity 90 of the body 88. A drawback of this design is that the back pressure is slow to react to a changing front pressure. The CE 92 has its sides sealed by the sealant 94 to prevent the gas from diffusing out the side of the WE 82 and reacting with the CE 92.

FIG. 5 is a cross-sectional view of a portion of another electrochemical cell where the sides of the porous WE 100 are sealed by a sealant 102, such as epoxy, to prevent the gas from exiting out the sides and affecting other electrodes. The CE 92 also has its sides sealed by the sealant 94, as described with respect to FIG. 4. The side sealants may be applied by needle dispense, jetting, printing, or other method prior to or after the electrodes are bonded to the body 88. Alternatively, the side sealants may be applied to the electrodes prior to their singulation, such as by printing. In this case, the electrode sides are sealed prior to being bonded to the body 88 and no further side sealing is required. Finally, the electrodes can be placed in individual cavities to isolate them from each other. This cavity-based separation provides alternative methods to increase structural support of the electrodes.

Sealing the sides of the electrodes also prevents fraying of the electrodes. The sealant may be any suitable polymer.

FIG. 6 illustrates another embodiment of a way to mechanical stabilize the WE100 to prevent flexure. FIG. 6 may be identical to FIG. 5 but the rigid body 88, such as a ceramic, directly contacts the back surface of the electrolyte layer 96, which may also be rigid like the electrolyte layer 80 in FIG. 3. This, in turn, supports the WE 100 in contact with the front surface of the electrolyte layer 96. Therefore, the rigid packaging itself is used to mechanically support the back surface of the WE 100 so as to prevent flexure.

In all embodiments, there may be separate cavities in the body 88 which contain at least a working electrode and a counter electrode. Each cavity and associated electrodes is independent and may be biased for a particular gas. All the cavities receive the ambient gas and each cavity may be dedicated to a particular target gas. A current sensor and microprocessor may use multiplexing to detect the various gasses sensed by the different cavities.

FIG. 7 is a cross-section of an electrochemical cell with an integrated shield layer and conductors for routing signals. The dielectric body 105, such as ceramic, is molded around a leadframe forming conductors 104 that conduct the sensing current and the bias voltages. The conductors 104 are complexly encased by the body material and run between the inner and outer walls of the body 105. The adhesive 86 that seals the gas and affixes the electrodes to the body may be a conductive adhesive and electrically contacts the WE 100. Other conductors are electrically connected to the CE 92 outside of the drawing. All the conductors 104 along each surface of the body 105 may be in the same plane. The conductors 104 are exposed at the top of the body 105 to form metal pads 106 for bonding (such as soldering) to a circuit board. Any number of pads 106 may be used.

The sensing current has a small signal-to-noise ratio, so any noise on the conductors 104 is significant. The conductors 104 are shielded from noise by a metal shield layer 108, which may be grounded or floating. The shield layer 108 is encased in the body 105. The shield layer 108 may be located around the top, bottom, and sides of the body 105, depending on the shielding requirements, to substantially surround the conductors 104. The shield layer 108 greatly reduces external noise being coupled to the bias signals and sensor current signals.

By embedding the conductors 104 within the body 105, they are protected from the electrolyte (e.g., a corrosive acid) and other possible damage. This allows the conductors 104 to be formed of virtually any type of highly conductive metal and allows the conductors 104 to be efficiently routed within the body 105.

While particular embodiments of the present invention have been shown and described, it will be obvious to those skilled in the art that changes and modifications may be made without departing from this invention in its broader aspects and, therefore, the appended claims are to encompass within their scope all such changes and modifications that are within the true spirit and scope of this invention.

What is claimed is:

1. An electrochemical gas sensor comprising:
 a body containing a cavity;
 an electrolyte contained within the cavity;
 a plurality of electrodes on the inside of the cavity, the electrodes being in contact with the electrolyte, the electrodes including a porous first electrode, such that a gas and the electrolyte enter the first electrode;

a gas opening in the body for allowing the gas to enter the first electrode to cause a chemical reaction to occur, the first electrode being supported within the cavity;

a first conductor electrically connected between the first electrode and a first metal pad on an outside surface of the body; and an electrically conductive adhesive that directly contacts the porous first electrode, affixes the first electrode to the body, forms an electrical connector between the first electrode and the first conductor, and also forms a gas seal around at least a portion of the first electrode, wherein the adhesive defines a gas cavity around the gas opening such that a surface of the porous first electrode extends along an entire surface of the gas cavity opposing the gas opening.

2. The sensor of claim 1 wherein the conductive adhesive substantially covers an entire first surface of the first electrode except for a gas inlet area for rigidly affixing the first electrode to the body.

3. The sensor of claim 1 further comprising a gas passageway that allows the gas that enters the first electrode via a front surface of the first electrode to also enter the cavity and provide a gas pressure to an opposing back surface of the first electrode to substantially equalize gas pressures applied to the front surface and the back surface.

4. The sensor of claim 3 wherein the conductive adhesive is patterned to provide the gas passageway into the cavity.

5. The sensor of claim 3 wherein the first electrode is configured to allow the gas to diffuse out of a side of the first electrode and into the cavity.

6. The sensor of claim 1 wherein the gas enters a front surface of the first electrode, the sensor further comprising a substantially rigid electrolyte layer contacting a back surface of the first electrode for mechanically supporting the first electrode.

7. The sensor of claim 1 wherein side surfaces of the first electrode are sealed to prevent the gas from exiting the side surfaces of the first electrode.

8. The sensor of claim 1 further comprising a porous second electrode within the cavity, side surfaces of the second electrode being sealed to prevent the gas from entering the side surfaces of the second electrode.

9. The sensor of claim 8 wherein the first electrode is a working electrode and the second electrode is a counter electrode.

10. The sensor of claim 1 wherein a first adhesive is infused through sides of the first electrode to add mechanical stability to the first electrode.

11. The sensor of claim 1 wherein the first electrode is positioned with respect to the gas opening to receive the gas into a front surface of the first electrode, and the electrolyte forms an electrolyte layer in contact with a back surface of the first electrode, the electrolyte layer having a back surface, the sensor further comprising:

a mechanical support portion, the electrolyte layer being between the first electrode and the mechanical support portion, the mechanical support portion contacting the back surface of the electrolyte layer to, in turn, mechanically support the first electrode.

12. The sensor of claim 1 wherein the first conductor is embedded within the body.

13. The sensor of claim 12 further comprising a metal shield layer between at least a portion of the first conductor and an outer surface of the body, the metal shield layer being embedded within the body.

14. The sensor of claim 1 wherein side surfaces of the first electrode are sealed by a polymer.

15. The sensor of claim 1 further comprising:

a metal shield layer encased within the walls of the body, the metal shield layer being located between the conductors and at least one outer wall of the body.

* * * * *